US012746340B2

(12) United States Patent
Gunzel et al.

(10) Patent No.: US 12,746,340 B2
(45) Date of Patent: Sep. 29, 2026

(54) FORMULATIONS, METHODS, AND PRE-FILLED MULTI-DOSE INJECTION DEVICES WITHOUT CLOUD POINT

(71) Applicant: W. L. Gore & Associates, Inc., Newark, DE (US)

(72) Inventors: Edward C. Gunzel, Oxford, PA (US); Thomas W. Patapoff, Captain Cook, HI (US)

(73) Assignee: W. L. Gore & Associates, Inc., Newark, DE (US)

( * ) Notice: Subject to any disclaimer, the term of this patent is extended or adjusted under 35 U.S.C. 154(b) by 670 days.

(21) Appl. No.: 18/037,129

(22) PCT Filed: Nov. 15, 2021

(86) PCT No.: PCT/US2021/072414
§ 371 (c)(1),
(2) Date: May 16, 2023

(87) PCT Pub. No.: WO2022/104389
PCT Pub. Date: May 19, 2022

(65) Prior Publication Data

US 2024/0017016 A1 Jan. 18, 2024

Related U.S. Application Data

(60) Provisional application No. 63/114,187, filed on Nov. 16, 2020.

(51) Int. Cl.
*A61M 5/315* (2006.01)
*A61M 5/31* (2006.01)

(52) U.S. Cl.
CPC ...... *A61M 5/31595* (2013.01); *A61M 5/3129* (2013.01); *A61M 2005/3131* (2013.01); *A61M 2205/0216* (2013.01)

(58) Field of Classification Search
CPC ............ A61M 5/31595; A61M 5/3129; A61M 2005/3131; A61M 2205/0216
See application file for complete search history.

(56) References Cited

U.S. PATENT DOCUMENTS

2006/0029635 A1 2/2006 Siebold et al.
2011/0137263 A1 6/2011 Ashmead et al.
(Continued)

FOREIGN PATENT DOCUMENTS

CA 3130457 A1 9/2020
CN 102725012 A 10/2012
(Continued)

OTHER PUBLICATIONS

"Protect Your Drug, Protect Your Patient", West FluroTec, Retrieved from the link: "https://adelphi-hp.com/assets/files/West/FluroTec%20Brochure.pdf" 2013, pp. 1-2.
(Continued)

*Primary Examiner* — Dung T Ulsh
(74) *Attorney, Agent, or Firm* — Faegre Drinker Biddle & Reath LLP

(57) ABSTRACT

The present disclosure is directed to pre-filled multi-dose injection devices and related therapeutic formulations and methods that lack a cloud point. The therapeutic formulation may be a transparent solution, and preservatives may remain within the aqueous phase without being phase separated to retain antimicrobial effectiveness.

20 Claims, 3 Drawing Sheets

(56) References Cited

U.S. PATENT DOCUMENTS

| | | | | |
|---|---|---|---|---|
| 2014/0031366 | A1 | 1/2014 | Andersson et al. | |
| 2017/0203043 | A1* | 7/2017 | Rusch | A61M 5/31513 |
| 2020/0054834 | A1 | 2/2020 | Berg et al. | |
| 2020/0308390 | A1 | 10/2020 | Phan et al. | |
| 2023/0414878 | A1 | 12/2023 | Gunzel et al. | |
| 2024/0252756 | A1 | 8/2024 | Berg et al. | |

FOREIGN PATENT DOCUMENTS

| | | | | |
|---|---|---|---|---|
| CN | 110325235 | A | 10/2019 | |
| EP | 2493534 | B1 | 4/2017 | |
| JP | 2002-020310 | A | 1/2002 | |
| JP | 2009-235075 | A | 10/2009 | |
| JP | 2012-051891 | A | 3/2012 | |
| JP | 2013-509270 | A | 3/2013 | |
| JP | 2013-545819 | A | 12/2013 | |
| JP | 2017-516870 | A | 6/2017 | |
| JP | 2020-508177 | A | 3/2020 | |
| WO | 97/48414 | A1 | 12/1997 | |
| WO | 01/03741 | A1 | 1/2001 | |
| WO | 2011/059823 | A1 | 5/2011 | |
| WO | WO-2011119487 | A2 * | 9/2011 | A61K 47/26 |
| WO | 2012/083138 | A2 | 6/2012 | |
| WO | 2015/187087 | A2 | 12/2015 | |
| WO | WO-2017123840 | A1 * | 7/2017 | A61M 5/31513 |
| WO | 2018/157097 | A1 | 8/2018 | |
| WO | 2019/173083 | A1 | 9/2019 | |
| WO | 2020/180850 | A1 | 9/2020 | |

OTHER PUBLICATIONS

Eester, "The Next Generation of Coated Plungers", ONdrugDelivery Magazine, Retrieved from the link: "https://ondrugdelivery.com/the-next-generation-of-coated-plungers", May 2020, pp. 1-6.

International Preliminary Report on Patentability received for PCT Patent Application No. PCT/US2021/072413, mailed on May 25, 2023, 7 pages.

International Preliminary Report on Patentability received for PCT Patent Application No. PCT/US2021/072414, mailed on May 25, 2023, 12 pages.

Irving, "Commercial Prefilled Syringe Filling", BioProcess International, Retrieved from the link: "https://www.bioprocessintl.com/sponsored-content/commercial-prefilled-syringe-filling", Aug. 16, 2014.

Haddou et al., "Cloud point extraction of phenol and benzyl alcohol from aqueous stream", Separation and Purification Technology, Elsevier Science, Amsterdam, NL, vol. 50, No. 1, Jun. 1, 2006 (Jun. 1, 2006), pp. 114-121, XP028035355.

International Search Report and Written Opinion received for PCT Patent Application No. PCT/US2021/072413, mailed on Mar. 21, 2022, 8 pages.

International Search Report and Written Opinion received for PCT Patent Application No. PCT/US2021/072414, mailed on Feb. 24, 2022, 15 pages.

Michael et al., "Considerations for the Use of Polysorbates in Biopharmaceuticals", Pharmaceutical Research, vol. 35, No. 2018, pp. 1-8.

* cited by examiner

FORMULATIONS, METHODS, AND PRE-FILLED MULTI-DOSE INJECTION DEVICES WITHOUT CLOUD POINT

CROSS-REFERENCE TO RELATED APPLICATION

This application is a national phase application of PCT Application No. PCT/US2021/072414, internationally filed on Nov. 15, 2021, which claims the benefit of U.S. Provisional No. 63/114,187, filed Nov. 15, 2021, which are herein incorporated by reference in their entireties for all purposes.

FIELD

The present disclosure relates generally to pre-filled multi-dose injection devices, and in particular, to pre-filled multi-dose injection devices and related therapeutic formulations and methods that lack a cloud point.

BACKGROUND

Pre-filled injection devices function to both store and deliver therapeutic formulations including drugs and/or biologics. Pre-filled injection devices generally offer cost savings to the pharmaceutical industry and may improve the safety, convenience, and efficacy of drug delivery. Biopharmaceuticals are an important class of pharmaceuticals that may increase the use of pre-filled injection devices, including syringes, and auto injectors. As more pharmaceuticals and particularly biopharmaceuticals are utilized for delivery in pre-filled injection devices, the use of conventional pre-filled technology presents several challenges.

One challenge is the use of silicone (e.g., silicone oil) and/or other liquid lubricants. Conventionally, silicone provides a liquid seal between the stopper and the barrel. While silicone has traditionally been used to ensure that the force required to actuate a pre-filled injection device is minimized, the use of silicone as a lubricant poses a contamination risk. For example, silicone may contaminate the drug or biologic within the injection device. Additionally, the silicone may be injected into a patient along with the drug. Silicone may be of particular concern with biopharmaceuticals because it can cause aggregation of certain proteins, thereby rendering the biopharmaceutical unusable for injection.

Another challenge is the use of polysorbate and/or other surfactants that contain fatty acid esters. Conventionally, surfactants reduce the effect of protein adsorption to the silicone oil and/or reduce interfacial tension. However, such surfactants may interact with preservatives and other excipients and cause the formulation to undergo a phase separation at a cloud point, transitioning from a transparent solution to a turbid solution. In practice, this turbidity may be indistinguishable from bacterial contamination, thus rendering the therapeutic formulation unusable.

Therefore, a need exists for formulations, methods, and pre-filled multi-dose injection devices that lack a cloud point.

SUMMARY

The present disclosure is directed to pre-filled multi-dose injection devices and related therapeutic formulations and methods that lack a cloud point. The therapeutic formulation may be a transparent solution, and preservatives may remain within the aqueous phase without being phase separated to retain antimicrobial effectiveness.

According to one example ("Example 1"), a pre-filled multi-dose injectable device is provided including a stopper, a barrel, a solid lubricant on at least one of the stopper and the barrel, the pre-filled multi-dose injectable device being free or substantially free of a liquid lubricant, and at least one formulated therapeutic including an active pharmacological agent and at least one phenolic or benzyl alcohol preservative, wherein the at least one formulated therapeutic is free or substantially free of a surfactant and exhibits a turbidity increase of less than 30 nephelometric turbidity units (NTU) upon warming from 5° C. to 30° C.

According to another example ("Example 2"), a method of reducing cloud point is provided, the method including incorporating a formulated therapeutic into a pre-filled multi-dose injectable device including a stopper, a barrel, and a solid lubricant on at least one of the stopper and the barrel, the pre-filled multi-dose injectable device being free or substantially free of a liquid lubricant, wherein the formulated therapeutic is free or substantially free of a surfactant and exhibits a turbidity increase of less than 30 nephelometric turbidity units (NTU) upon warming from 5° C. to 30° C., and wherein the formulated therapeutic includes an active pharmacological agent and at least one phenolic or benzyl alcohol preservative.

According to yet another example ("Example 3"), a multi-dose parenteral formulation is provided including an active pharmacological agent and at least one phenolic or benzyl alcohol preservative, wherein the multi-dose parenteral formulation is free or substantially free of a surfactant and exhibits a turbidity increase of less than 30 nephelometric turbidity units (NTU) upon warming from 5° C. to 30° C.

The foregoing Examples are just that and should not be read to limit or otherwise narrow the scope of any of the inventive concepts otherwise provided by the instant disclosure. While multiple examples are disclosed, still other embodiments will become apparent to those skilled in the art from the following detailed description, which shows and describes illustrative examples. Accordingly, the drawings and detailed description are to be regarded as illustrative in nature rather than restrictive in nature.

BRIEF DESCRIPTION OF THE DRAWINGS

The present invention will be better understood in view of the following non-limiting figures, in which.

DETAILED DESCRIPTION

Definitions and Terminology

This disclosure is not meant to be read in a restrictive manner. For example, the terminology used in the application should be read broadly in the context of the meaning those in the field would attribute such terminology.

With respect to terminology of inexactitude, the terms "about" and "approximately" may be used, interchangeably, to refer to a measurement that includes the stated measurement and that also includes any measurements that are reasonably close to the stated measurement. Measurements that are reasonably close to the stated measurement deviate from the stated measurement by a reasonably small amount as understood and readily ascertained by individuals having ordinary skill in the relevant arts. Such deviations may be attributable to measurement error, differences in measurement and/or manufacturing equipment calibration, human error in reading and/or setting measurements, minor adjustments made to optimize performance and/or structural parameters in view of differences in measurements associated with other components, particular implementation scenarios, imprecise adjustment and/or manipulation of objects by a person or machine, and/or the like, for example. In the event it is determined that individuals having ordinary skill in the relevant arts would not readily ascertain values for such reasonably small differences, the terms "about" and "approximately" can be understood to mean plus or minus 10% of the stated value.

Description of Various Embodiments

Persons skilled in the art will readily appreciate that various aspects of the present disclosure can be realized by any number of methods and apparatus configured to perform the intended functions. It should also be noted that the accompanying drawing figures referred to herein are not necessarily drawn to scale and may be exaggerated to illustrate various aspects of the present disclosure, and in that regard, the figures should not be construed as limiting.

I. Multi-Dose Injection Device

Figure 1:
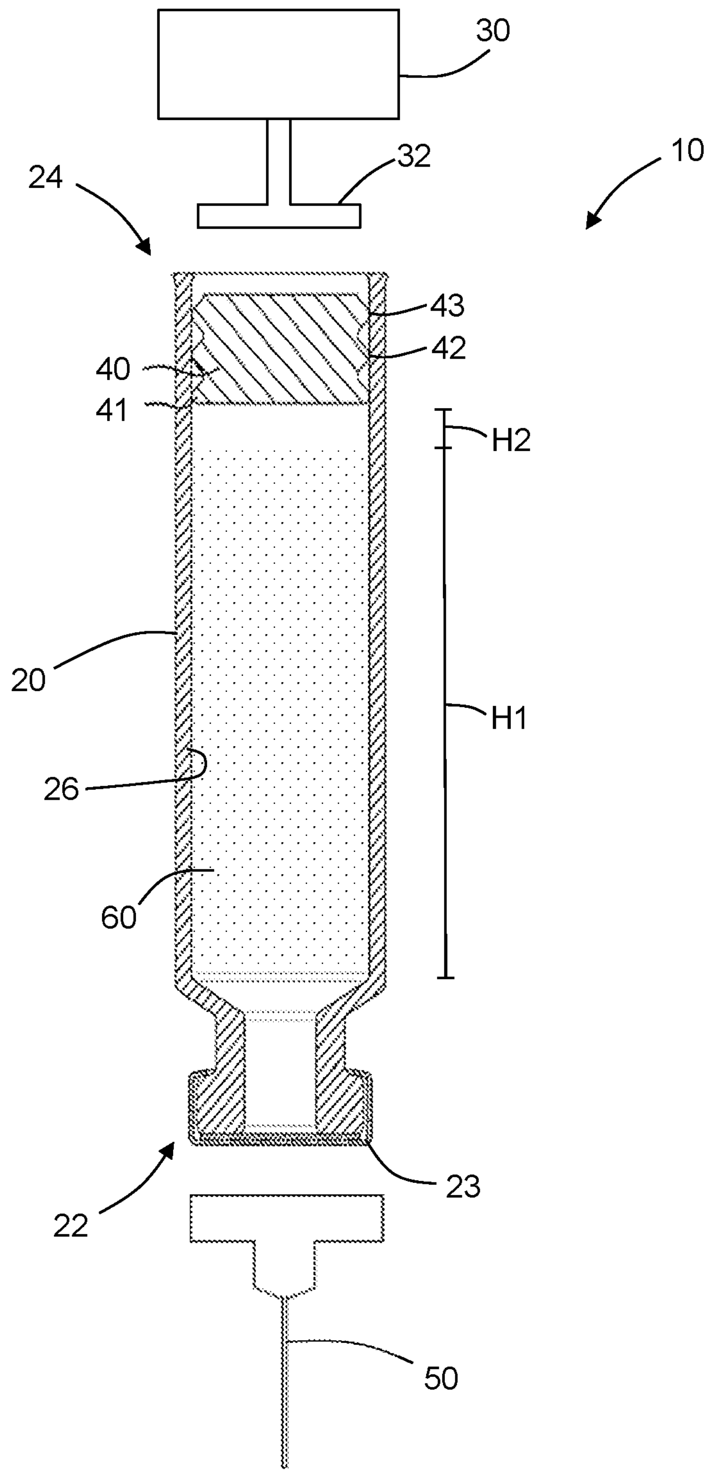
FIG. 1 is an elevational view of an exemplary pre-filled syringe including a barrel, an actuator, a stopper, a needle, and a therapeutic formulation in accordance with at least one embodiment.

FIG. 1 depicts a drug injection device 10 that may be pre-filled for storing and delivering at least one therapeutic formulation 60 to a patient. The illustrative device 10 includes a housing (not shown), a cartridge or barrel 20, an actuator 30, a stopper 40, and a piercing element (e.g., needle) 50, each of which is described further below. The device 10 may be in the form of an auto-injector or an injectable pen, for example.

The barrel 20 of the device 10 contains the liquid therapeutic formulation 60. The barrel 20 is removably coupled to the housing and includes a distal end 22 that faces toward the patient, a proximal end 24 that faces away from the patient, and an inner surface 26 that faces inward toward the liquid therapeutic formulation 60. In FIG. 1, the distal end 22 of the barrel 20 is covered by a pierceable cap 23. The proximal end 24 of the barrel 20 may also be covered until it is loaded into the housing and/or exposed to the actuator 30. The barrel 20 may be formed of a hard material, such as a glass material (e.g., borosilicate glass), a ceramic material, one or more polymeric materials (e.g., polypropylene, polyethylene, and copolymers thereof), a metallic material, a plastic material (e.g., cyclic olefin polymers and cyclic olefin copolymers), and combinations thereof. In some embodiments, the barrel 20 has already been pre-filled with the therapeutic formulation 60 upon delivery to the user. The barrel 20 may contain about 0.5 mL to about 20 mL of the therapeutic formulation 60, but the device 10 may also be appropriately scaled to smaller doses or larger, multi-doses.

The actuator 30 is removably coupled to the proximal end 24 of the barrel 20. The actuator 30 may include a plunger 32 that is movable within the barrel 20 to discharge the therapeutic formulation 60 by moving the stopper 40. The actuator 30 may include a dose selector (e.g., a dial) (not shown) that controls the distance traveled by the plunger 32 and a trigger (e.g., a button) (not shown) that initiates movement of the plunger 32. The stopper 40 contacts the inner surface 26 of the barrel 20 via one or more sealing ribs 41, 42, 43, although any number of sealing ribs and/or non-sealing ribs may be present on the stopper 40.

As shown in FIG. 1, the stopper 40 may be positioned at a predetermined location in the barrel 20 relative to the therapeutic formulation 60. The therapeutic formulation 60 has a liquid height H1, which depends on the volume of the therapeutic formulation 60 in the barrel 20. The stopper 40 may be located at a predetermined stopper height or "headspace" H2 above the therapeutic formulation 60, which may be measured from the top surface of the therapeutic formulation 60 to the nearest sealing rib 41 of the stopper 40. Although the illustrative stopper 40 of FIG. 1 has a flat bottom surface near sealing rib 41, it is also within the scope of the present disclosure for the bottom surface to have a conical shape that extends downward past the sealing rib 41. The headspace H2 may be selected to control the amount of air in the barrel 20 between the stopper 40 and the therapeutic formulation 60. In some embodiments, the headspace H2 is less than about 25 mm, less than about 23 mm, less than about 21 mm, less than about 19 mm, less than about 17 mm, less than about 15 mm, less than about 13 mm, less than about 10 mm, less than about 8 mm, less than about 5 mm, less than about 3 mm, less than about 2 mm, less than about 1 mm, or less than about 0.5 mm. The headspace volume may be calculated by multiplying the headspace height H2 by the interior cross-sectional area of the barrel 20, less any volume of the stopper 40 that extends past the sealing rib 41 of the stopper 40 toward the therapeutic formulation 60. It may be advantageous to minimize the headspace H2 to reduce or avoid aggregation of the therapeutic formulation 60 in the device 10.

The stopper 40 should have low air and liquid permeability to minimize liquid leakage within the barrel 20 and the introduction of air between the stopper 40 and the inner surface 26 of the barrel 20 when charging or discharging the therapeutic formulation 60. In this way, the stopper 40 may resist bacterial contamination in the barrel 20. The stopper 40 should also possess low-friction slidability relative to the barrel 20 to facilitate the charging and discharging of the therapeutic formulation 60 inside the barrel 20. In some embodiments, the slide force between the stopper 40 and the barrel 20 may be less than 15 N, less than 10 N, or less than 5 N. The stopper 40 is described further in Section II below.

The needle 50 of the device 10 is removably coupled to the distal end 22 of the barrel 20, such as using a Luer system. The needle 50 is configured to pierce the patient's skin and inject the therapeutic formulation 60 into the patient when operating the actuator 30. Care should be taken to minimize any bacterial contamination in the barrel 20 when coupling the needle 50 to the barrel 20 and/or when uncoupling the needle 50 from the barrel 20.

The interior of the device 10 (not including the needle 50, as explained below) is free of liquid lubricants (i.e., "lubricant free") or substantially free of liquid lubricants (i.e., "substantially lubricant free"). In particular, the barrel 20 and the stopper 40 of the device 10 are free or substantially free of silicone (e.g., silicone oil, silicone grease). As used herein, the phrases "lubricant free" and "free of a liquid lubricant" mean that the barrel 20 and the stopper 40 contain no liquid lubricant of any kind, either intentionally or accidentally (i.e., 0 picograms (pg) of lubricants), or contain only a trace amount of liquid lubricant that is undetectable by any known measuring equipment or method. The phrases "substantially lubricant free" and "substantially free of a liquid lubricant" mean that the barrel 20 and the stopper 40 contain an insignificant but measurable amount of liquid lubricants, such as about 5 μg or less, about 4 μg or less, about 3 μg or less, about 2 μg or less, or about 1 μg or less. In certain embodiments, liquid lubricants are present on the barrel 20 and/or the stopper 40 from 0 μg to about 5 μg, from about 1 μg to about 5 μg, from about 2 μg to about 5 μg, from about 3 μg to about 5 μg, or from about 4 μg to about 5 μg. The absence or substantial absence of liquid lubricants can be measured using gas chromatography (GC) mass spectrometry, inductively coupled plasma (ICP) mass spectrometry, and/or by the amount of particles in the barrel 20 that are measured in water for injection (WFI) after the WFI has been exposed to a fully assembled syringe (e.g., a glass barrel 20 and stopper 40 and alternatively at least one therapeutic compound). In some embodiments, the amount of particles in the barrel 20 may be less than about 600 particles/ml for particles greater than 10 pm in size or less than 60 particles/ml for particles greater than 25 pm in size when measured in WFI. The needle 50 of the device 10 may have a lubricant to ease insertion into the patient's skin without impacting the ability for the rest of the device 10 to be free "lubricant free" or "substantially lubricant free", as described above.

II. Stopper

Figure 2:
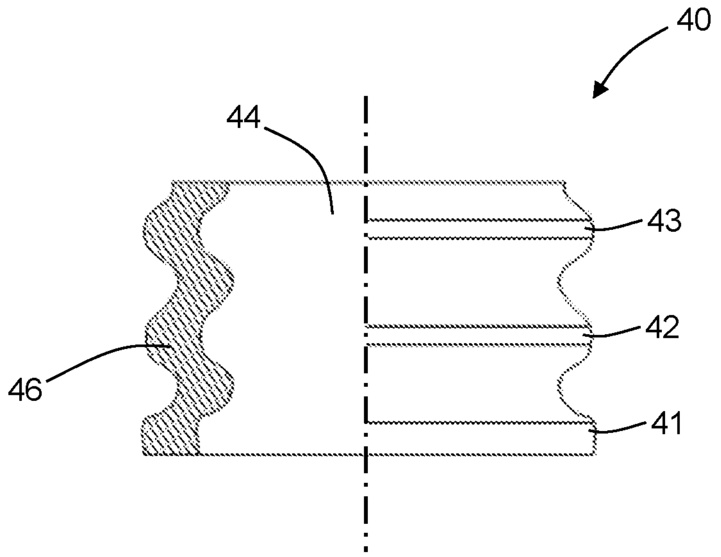
FIG. 2 is a partial cutaway view of the stopper of FIG. 1 having an elastomeric body at least partially covered by a solid lubricant layer in accordance with at least one embodiment.

Referring next to FIG. 2, the stopper 40 is shown in more detail and includes an elastomeric body 44 at least partially covered by a solid lubricant layer 46. The solid lubricant layer 46 may be designed to provide a low coefficient of friction with the barrel 20 (FIG. 1), compliance, low extractables and leachables (in particular, low metal-ion extractables and leachables), and/or good barrier properties against any extractables and leachables in the elastomeric body 44.

The elastomeric body 44 of the stopper 40 may comprise any suitable elastomer, such as butyl rubber, bromobutyl rubber, chlorobutyl rubber, silicone, nitrile, styrene butadiene, polychloroprene, ethylene propylene diene, fluoroelastomers and combinations thereof. In other embodiments, the stopper 40 may be constructed of non-elastomeric materials, such as plastics (e.g., polypropylene, polycarbonate, and polyethylene), thermoplastics, and fluoropolymer materials such as ethylene-(perfluoro-ethylene-propene) copolymer (EFEP), polyvinylidene difluoride (PVDF), and perfluoroalkoxy polymer resin (PFA).

The solid lubricant layer 46 of the stopper 40 may comprise a low coefficient of friction polymer layer, which may have a coefficient of friction of about 0.08 to about 0.8 against the glass of the barrel 20. The solid lubricant layer 46 may be constructed of a fluoropolymer including, but not limited to, polytetrafluoroethylene (PTFE), expanded polytetrafluoroethylene (ePTFE), densified ePTFE, and copolymers and combinations thereof. Other materials for use as the solid lubricant layer 46 include, but are not limited to, fluorinated ethylene propylene (FEP), ethylene tetrafluoroethylene (ETFE), polyvinylfluoride, polyvinylidene fluoride (e.g., poly(vinylidene fluoride-co-tetrafluoroethylene) (VDF-co-TFE), poly(vinylidene fluoride-co-trifluoroethylene) (VDE-co-TrFE)), perfluoropropylvinylether, perfluoroalkoxy polymers, polyethylene (e.g., expanded ultra-high molecular weight polyethylene (eUHMWPE)), polypropylene, poly (p-xylylene) (PPX), polylactic acid (PLA), poly (L-lactic acid) (PLLA), poly(D-lactic acid) (PDLA), and copolymers and combinations thereof, which may be expanded if desired.

The stopper 40 of FIG. 2 may be manufactured by thermoforming the solid lubricant layer 46 from a densified ePTFE film and then molding (e.g., injection molding, compression molding) the elastomeric body 44 onto the thermoformed solid lubricant layer 46. In another embodiment, the stopper 40 of FIG. 2 may be manufactured by a direct molding process, in which a sheet of the solid lubricant layer 46 is placed in a heated mold together with the material for elastomeric body 44 to simultaneously vulcanize the elastomeric body 44, if applicable, and form the stopper 40. It is also within the scope of the present disclosure to pre-treat or post-treat the solid lubricant layer 46 with chemical etching, plasma treating, corona treatment, roughening, or the like to improve the bonding of the solid lubricant layer 46 to the elastomeric body 44.

Figure 3:
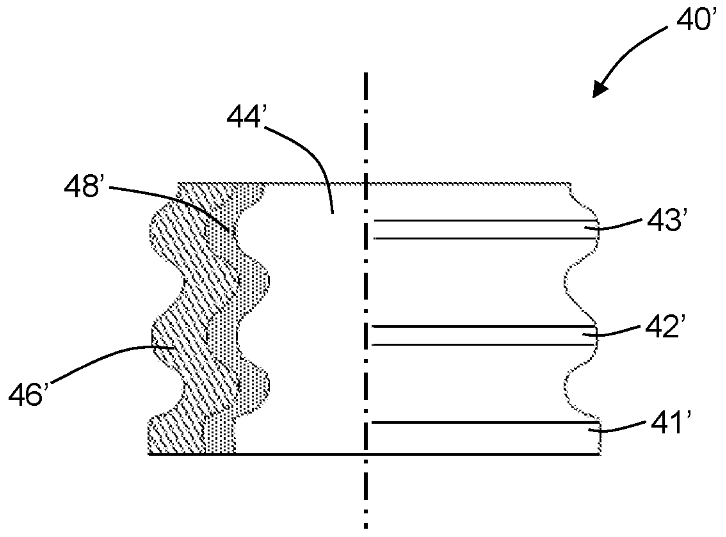
FIG. 3 is a partial cutaway view of another stopper having an elastomeric body, an intermediate porous layer, and a solid lubricant in accordance with at least one embodiment.

Referring next to FIG. 3, another stopper 40' is shown, with like reference numerals identifying like elements. The stopper 40' includes an elastomeric body 44' and a solid lubricant layer 46' (also referred to as a barrier layer), as well as an intermediate porous layer 48'. The porous layer 48' may comprise or be formed of ePTFE or other porous expanded and advantageously fibrillizing fluoropolymers. The adjacent elastomeric body 44' and/or solid lubricant layer 46' may at least partially penetrate the intermediate porous layer 48', and the degree of penetration may be controlled to achieve desired strength, toughness, compliance and stability for the desired application.

The stopper 40' of FIG. 3 may be manufactured by forming the porous layer 48', coating, laminating, imbibing, or otherwise applying the solid lubricant layer 46' onto and/or into the porous layer 48' to create a multi-layered or composite film, and then molding (e.g., injection molding, compression molding) the elastomeric body 44' onto the film such that the elastomeric body 44' at least partially penetrates the pores of the porous layer 48'. It is also within the scope of the present disclosure to pre-treat or post-treat the solid lubricant layer 46' and/or the porous layer 48' with chemical etching, plasma treating, corona treatment, roughening, or the like to improve the bonding of the solid lubricant layer 46' to the elastomeric body 44'.

III. Therapeutic Formulation

Figure 4:
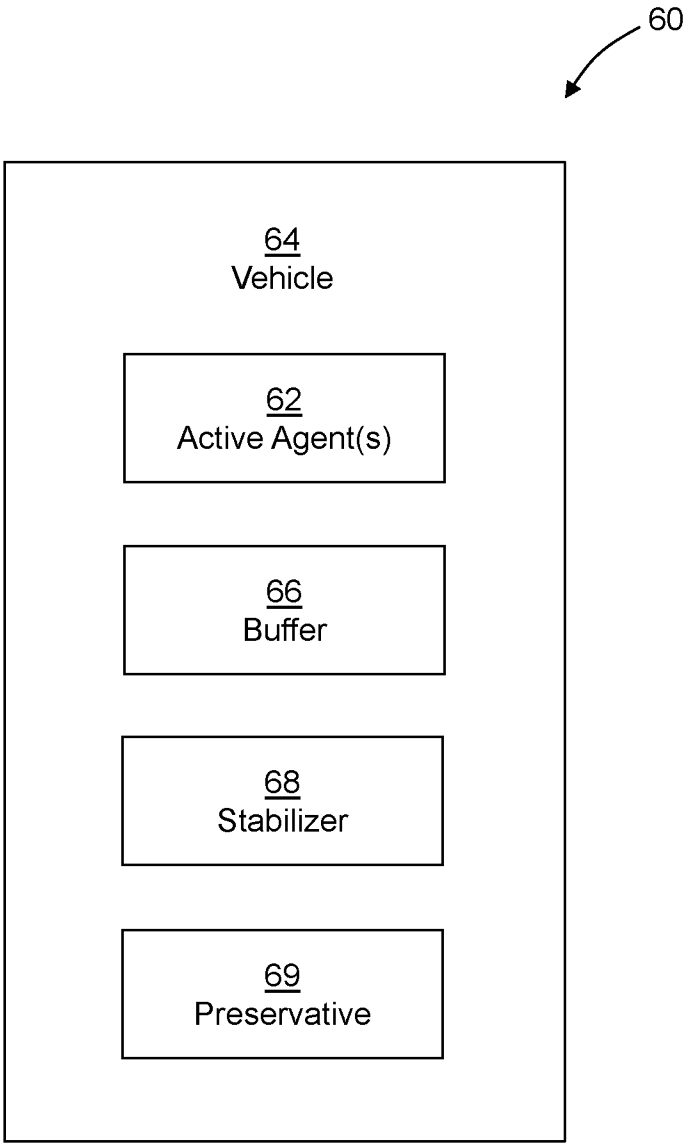
FIG. 4 is a schematic view of the therapeutic formulation of FIG. 1 in accordance with at least one embodiment.

The therapeutic formulation 60 is shown schematically in FIG. 4. The therapeutic formulation 60 may be a multi-dose formulation (which may also be referred to as a multi-use formulation) that is intended to be delivered to the patient in multiple doses over time. As noted above, the multi-dose therapeutic formulation 60 may be present in a larger volume than a comparable single-dose formulation.

The therapeutic formulation 60 includes one or more active pharmacological agents 62, more specifically active biopharmaceuticals agents. The active agents 62 may be used for use in the treatment of inflammatory diseases including, but not limited to, inrheumatoid arthritis (RA), psoriasis, inflammatory bowel disease (IBD), and ocular inflammatory disease. Active agents 62 include, but are not limited to, proteins, antibodies, cytokines, insulin, insulin analogs, growth hormones, growth factors, coagulation factors, proteases, kinases, phosphatases, vaccines, peptides, small interfering RNAs (siRNAs), small interfering DNAs (siDNAs), messenger RNAs (mRNAs), aptamers, and/or any combination thereof. The active agent(s) 62 may be present in the therapeutic formulation 60 at a concentration of at least about 1 mg/ml, such as a concentration from about 1 mg/ml to about 200 mg/ml, from about 10 mg/ml to about 200 mg/ml, from about 20 mg/ml to about 200 mg/ml, from about 40 mg/ml to about 200 mg/ml, from about 60 mg/ml to about 200 mg/ml, from about 80 mg/ml to about 200 mg/ml, from about 100 mg/ml to about 200 mg/ml, from about 120 mg/ml to about 200 mg/ml, and/or from about 150 mg/ml to about 200 mg/ml. Specific active agents 62 are set forth in Section IV below.

The therapeutic formulation 60 of FIG. 4 also includes a vehicle 64 (e.g., solvent, diluent) capable of conveying the active agent 62 to the patient during injection. Suitable solvents include, for example, water, acetic acid, propylene glycol, ethylene glycol, polyethylene glycol, benzyl benzoate, and combinations thereof.

The therapeutic formulation 60 may also include one or more excipients. The excipients may be configured to protect, support, or enhance processability, stability, sterility, bioavailability, product identification, effectiveness, delivery, and/or storage integrity.

One excipient is a buffer 66 including, for example, phosphate (e.g., phosphate buffered saline (PBS), acetate, histidine, and tris. The buffer 66 may have a pH from about 4.0 to about 9.5, from about 4.5 to about 9.0, from about 5.0 to about 8.5, from about 5.5 to about 8.0, from about 5.5 to about 7.5, from about 5.5 to about 7.0, and/or from about 5.5 to about 6.5.

Another excipient is a stabilizer 68 including, for example, sugars (e.g., sucrose, trehalose, maltose, and lactose), polyols (e.g., mannitol, sorbitol, and glycerol), and amino acid salts (e.g., histidine, arginine, and glycine). The concentration of sugar in the therapeutic formulation 60 may be from 0 wt. % to about 15 wt. %, from about 0.1 wt. % to about 15 wt. %, from about 1 wt. % to about 15 wt. %, from about 1.5 wt. % to about 10 wt. %, from about 2 wt. % to about 10 wt. %, from about 3 wt. % to about 10 wt. %, and/or from about 5 wt. % to about 10 wt. %. The concentration of polyol in the therapeutic formulation 60 may be from 0 wt. % to about 5 wt. %, from about 0.1 wt. % to about 5 wt. %, from about 1 wt. % to about 5 wt. %, from about 1.5 wt. % to about 5 wt. %, from about 2 wt. % to about 5 wt. %, and/or from about 3 wt. % to about 5 wt. %. The concentration of amino acid salts in the therapeutic formulation 60 may be from 0 wt. % to about 5 wt. %, from about 0.1 wt. % to about 5 wt. %, from about 1 wt. % to about 5 wt. %, from about 1.5 wt. % to about 5 wt. %, from about 2 wt. % to about 5 wt. %, and/or from about 3 wt. % to about 5 wt. %.

Yet another excipient is a preservative 69 having antimicrobial activity. Preservatives include, for example, phenolic preservatives (e.g., phenol, ortho-cresol, meta-cresol, para-cresol, propylparaben, methylparaben), benzyl alcohol preservatives (e.g., methylbenzyl alcohols), and/or any combination thereof. The concentration of preservatives 69 in the therapeutic formulation 60 may be from about 0.1 wt. % to about 5 wt. %, from about 0.1 wt. % to about 3 wt. %, from about 0.1 wt. % to about 1 wt. %, and/or from about 0.2 wt. % to about 0.8 wt. %.

The therapeutic formulation 60 of FIG. 4 is free of surfactants (i.e., "surfactant free") or substantially free of surfactants (i.e., "substantially surfactant free" or "substantially free of a surfactant"). In particular, the therapeutic formulation 60 is free or substantially free of polysorbate surfactants, including polysorbate 20, polysorbate 40, polysorbate 60, polysorbate 80, and combinations thereof. Such surfactants are generally used to lower surface tension and/or interfacial tension and prevent therapeutics from adsorbing onto surfaces and/or interfaces. As used herein, the phrase "surfactant free" means that the therapeutic formulation 60 contains no surfactants of any kind, either intentionally or accidentally (i.e., 0 wt. % surfactants), or contains only a trace amount of surfactants that is undetectable by any known measuring equipment or method. The phrase "substantially surfactant free" and "substantially free of a surfactant" mean that the therapeutic formulation 60 contains an insignificant but measurable amount of surfactants, such as about 0.1 wt. % or less, about 0.075 wt. % or less, about 0.05 wt. % or less, about 0.025 wt. % or less, about 0.01 wt. % or less, about 0.005 wt. % or less, or about 0.001 wt. % or less. In certain embodiments, the concentration of surfactants in the therapeutic formulation 60 may be from 0 wt. % to about 0.1 wt. %, from 0 wt. % to about 0.075 wt. %, from 0 wt. % to about 0.05 wt. %, from 0 wt. % to about 0.025 wt. %, from 0 wt. % to about 0.01 wt. %, from 0 wt. % to about 0.005 wt. %, and/or from 0 wt. % to about 0.001 wt. %.

The therapeutic formulation 60 of FIG. 4 also lacks a cloud point, even when heated to 30° C., 40° C., or 50° C., for example. The therapeutic formulation 60 remains transparent and avoids aggregation, precipitation, or decomposition of the preservative 69, in particular, which would pull the preservative 69 out of the aqueous phase and decrease the antimicrobial activity of the preservative 69. The therapeutic formulation 60 may retain at least about 80% of the preservative 69 in the solution after heating, such as about 80%, about 85%, about 90%, about 95%, about 99%, or about 100%. In terms of turbidity measured with a nephelometer, the therapeutic formulation 60 may exhibit a turbidity increase after heating of 30 nephelometric turbidity units (NTU) or less when heated, such as about 25 NTU, about 20 NTU, about 15 NTU, about 10 NTU, about 5 NTU, about 1 NTU, or about 0 NTU. In terms of apparent absorbance measured at a wavelength of 400 nm to 500 nm with a spectrometer, the therapeutic formulation 60 may exhibit an absorbance increase after heating of about 0.1 AU or less, such as about 0.1 AU, about 0.08 AU, about 0.06 AU, about 0.04 AU, about 0.02 AU, or about 0 AU.

IV. Active Agents

As noted above, the therapeutic formulation 60 includes one or more active agents 62, which may include biomolecules such as proteins, antibodies, cytokines, insulin, insulin analogs, growth hormones, growth factors, coagulation factors, proteases, kinases, phosphatases, vaccines, peptides, small interfering RNAs (siRNAs), small interfering DNAs (siDNAs), messenger RNAs (mRNAs), aptamers, and/or any combination thereof.

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

PROPHETIC EXAMPLES

Prophetic Example A: Impact of Surfactants on Cloud Point

Sample Preparation: Samples containing a buffer (e.g., 20 mM histidine chloride buffer, pH 6) will be prepared in 3 cc or larger glass vials. The samples will contain various preservative types (e.g., phenol, methylparaben, meta-cresol) and concentrations (e.g., 0 wt. %, 0.2 wt. %, 0.4 wt. %, 0.6 wt. %, 0.8 wt. %). The samples will also contain various polysorbate surfactants (e.g., polysorbate 20 (PS20) and polysorbate 80 (PS80)) and concentrations (e.g., 0 wt. %, 0.01 wt. %, 0.02 wt. %, 0.05 wt. %, 0.1 wt. %, 0.2 wt. %).

Heating: Each sample solution will be placed in a 1 cm pathway glass/quartz cuvette with a micro-stir bar and a thermocouple at the top of the solution. Each cuvette will be placed in a spectrophotometer with a temperature-controlled cuvette holder. Each sample will be stirred while equilibrating the solution at 15° C. and then heating the solution 1° C. per minute to 50° C. Once a cloud point is passed, each sample may be cooled back to 15° C. and the heating repeated.

Analysis: One suitable instrument is a spectrophotometer that measures apparent absorption at 400 nm-500 nm during the heating process to determine the temperature at which the apparent absorption increases rapidly. Another suitable instrument is a nephelometer that measures turbidity in nephelometric turbidity units (NTU) during the heating process to determine the temperature at which the turbidity increases rapidly.

Prophetic Results: For samples without the PS20 or PS80 surfactant, the present inventors believe that the samples will not exhibit a rapid increase in absorption (e.g., 0.1 AU or less) or turbidity (e.g., 30 NTU or less) during heating. For samples with the PS20 or PS80 surfactant, the present inventors believe that the samples will exhibit a rapid increase in absorption (e.g., 0.15 AU or more) or turbidity (e.g., 50 NTU or more), which is indicative of a cloud point.

Prophetic Example B: Effect of Cloud Point on Antimicrobial Effectiveness

Sample Preparation: The same samples from Example A are prepared and placed in 50 cc vials, with each sample having a volume of 30 mL.

Heating: Each sample is heated above its cloud point of Example A.

Centrifugation: Each clouded sample is centrifuged at that temperature to collect the supernatant and remove the turbid phase.

Analysis: Using an extinction coefficient from a standard curve, the supernatant is subjected to spectrophotometry to determine the preservative concentration that remains in the supernatant. Select samples may also be subjected to an Antimicrobial Effectiveness Test (AET) to evaluate the antimicrobial effectiveness of the preservative that is available in the aqueous phase.

Prophetic Results: The present inventors believe that the PS20 or PS80 surfactant concentration will have an indirect effect on the preservative concentration in the aqueous phase. For example, the present inventors believe that the samples containing PS20 or PS80 concentrations of 0.01 wt. % or more may lose more than about 20%, about 25%, or about 30%, of the preservative in the aqueous phase. The samples without PS20 or PS80 are expected to avoid phase separation altogether and thus retain all of the of the preservative in the aqueous phase.

What is claimed is:

1. A pre-filled multi-dose injectable device comprising:
a stopper;
a barrel;
a solid lubricant on at least one of the stopper and the barrel, the pre-filled multi-dose injectable device being free or substantially free of a liquid lubricant; and
at least one formulated therapeutic comprising:
an active pharmacological agent selected from small interfering RNAs (siRNAs), small interfering DNAs (siDNAs), messenger RNAs (mRNAs), aptamers, and/or a combination thereof; and
at least one phenolic or benzyl alcohol preservative;
wherein the at least one formulated therapeutic is free or substantially free of a surfactant, wherein the surfactant comprises at least one of polysorbate 20, polysorbate 40, polysorbate 60, polysorbate 80, or a combination thereof, and exhibits a turbidity increase of less than 30 nephelometric turbidity units (NTU) upon warming from 5° C. to 30° C.

2. The pre-filled multi-dose injectable device of claim 1, wherein the at least one formulated therapeutic includes the active pharmacological agent at a concentration from about 1 mg/ml to about 200 mg/ml, from about 10 mg/ml to about 200 mg/ml, from about 20 mg/ml to about 200 mg/ml, from about 50 mg/ml to about 200 mg/ml, from about 80 mg/ml to about 200 mg/ml, from about 100 mg/ml to mg/ml to about 200 mg/ml.

3. The pre-filled multi-dose injectable device of claim 1, wherein the at least one formulated therapeutic includes the surfactant at a concentration from 0 wt. % to about 0.1 wt. %, from 0 wt. % to about 0.075 wt. %, from 0wt. % to about 0.05 wt. %, from 0 wt. % to about 0.025 wt. %, from 0 wt. % to about 0.01wt. %, from 0 wt. % to about 0.005 wt. %, or from 0 wt. % to about 0.001 wt. %.

4. The pre-filled multi-dose injectable device of claim 1, wherein the at least one formulated therapeutic comprises a buffer having a pH from about 4.0 to about 9.5, from about 4.5 to about 9.0, from about 5.0 to about 8.5, from about 5.5 to about 8.0, from about 5.5 to about 7.5, from about 5.5 to about 7.0, or from about 5.5 to about 6.5.

5. The pre-filled multi-dose injectable device of claim 1, wherein the at least one formulated therapeutic comprises a sugar having a concentration from 0 wt. % to about 15 wt. %, from about 0.1 wt. % to about 15 wt. %, from about 1 wt. % to about 15 wt. %, from about 1.5 wt. % to about 10 wt. %, from about 2 wt. % to about 10 wt. %, from about 3 wt. % to about 10 wt. %, or from about 5 wt. % to about 10 wt. %.

6. The pre-filled multi-dose injectable device of claim 1, wherein the at least one formulated therapeutic comprises a polyol having a concentration from 0 wt. % to about 5 wt. %, from about 0.1 wt. % to about 5 wt. %, from about 1 wt. % to about 5 wt. %, from about 1.5 wt. % to about 5 wt. %, from about 2 wt. % to about 5 wt. %, or from about 3 wt. % to about 5 wt. %.

7. The pre-filled multi-dose injectable device of claim 1, wherein the at least one formulated therapeutic comprises an arginine salt having a concentration from 0 wt. % to about 5 wt. %, from about 0.1 wt. % to about 5 wt. %, from about 1 wt. % to about 5 wt. %, from about 1.5 wt. % to about 5 wt. %, from about 2 wt. % to about 5 wt. %, or from about 3 wt. % to about 5 wt. %.

8. The pre-filled multi-dose injectable device of claim 1, wherein the stopper and the barrel are free or substantially free of the liquid lubricant silicone.

9. The pre-filled multi-dose injectable device of claim 1, wherein the barrel is made of at least one of a glass material, a plastic material, a ceramic material, a metallic material, or a combination thereof.

10. The pre-filled multi-dose injectable device of claim 1, wherein the turbidity increase is from 0 NTU to about 25 NTU, from 0 NTU to about 20NTU, from 0 NTU to about 15 NTU, from 0 NTU to about 10 NTU, from 0 NTU to about 5 NTU, or from 0 NTU to about 1 NTU.

11. The pre-filled multi-dose injectable device of claim 1, wherein the turbidity increase is no more than about 20 NTU, no more than about 10NTU, no more than about 5 NTU, or no more than about 1 NTU.

12. The pre-filled multi-dose injectable device of claim 1, wherein the solid lubricant is a low coefficient of friction layer and the stopper comprises an elastomeric body and the low coefficient of friction layer positioned on the elastomeric body.

13. The pre-filled multi-dose injectable device of claim 12, wherein the low coefficient of friction layer comprises a fluoropolymer.

14. The pre-filled multi-dose injectable device of claim 13, wherein the fluoropolymer of the low coefficient of friction layer is an expanded fluoropolymer.

15. The pre-filled multi-dose injectable device of claim 14, wherein the elastomeric body is at least partially imbibed into the expanded fluoropolymer of the low coefficient of friction layer.

16. The pre-filled multi-dose injectable device of claim 14, wherein the expanded fluoropolymer of the low coefficient of friction layer is pre-treated with at least one treatment of chemical etching, plasma treating, corona, and physical modification.

17. The pre-filled multi-dose injectable device of claim 13, wherein the fluoropolymer of the low coefficient of friction layer is an expanded polytetrafluoroethylene (ePTFE).

18. The pre-filled multi-dose injectable device of claim 13, wherein the fluoropolymer of the low coefficient of friction layer comprises a composite fluoropolymer film having a barrier layer and a porous layer, the barrier layer comprising at least one of polytetrafluoroethylene (PTFE), expanded polytetrafluoroethylene (ePTFE), densified ePTFE, fluorinated ethylene propylene (FEP), ethylene tetrafluoroethylene (ETFE), polyvinylfluoride, polyvinylidene fluoride, perfluoropropylvinylether, perfluoroalkoxy polymers, polyethylene, polypropylene, poly (p-xylylene) (PPX), polylactic acid (PLA), poly (L-lactic acid) (PLLA), poly (D-lactic acid) (PDLA), and copolymers and combinations thereof.

19. The pre-filled multi-dose injectable device of claim 1, comprising a plunger rod movable in the barrel and configured to move the stopper.

20. The pre-filled multi-dose injectable device of claim 1, wherein the at least one phenolic or benzyl alcohol preservative is selected from:

a) a phenolic preservative comprising phenol, orthocresol, metacresol, para-cresol, propylparaben, methylparaben;

b) a benzyl alcohol preservative comprising methylbenzyl alcohols; or c) any combination of the foregoing phenolic and benzyl alcohol preservatives.

* * * * *